US012729227B2

(12) United States Patent
Bleck et al.

(10) Patent No.: US 12,729,227 B2
(45) Date of Patent: Sep. 8, 2026

(54) DECORIN COMPOSITIONS AND USE THEREOF

(71) Applicant: Catalent Pharma Solutions LLC, Somerset, NJ (US)

(72) Inventors: Gregory T. Bleck, Cross Plains, WI (US); Ian John Collins, Sauk City, WI (US); Mark Joseph Frey, Lodi, WI (US)

(73) Assignee: Catalent Pharma Solutions LLC, Somerset, NJ (US)

( * ) Notice: Subject to any disclaimer, the term of this patent is extended or adjusted under 35 U.S.C. 154(b) by 172 days.

(21) Appl. No.: 17/366,284

(22) Filed: Jul. 2, 2021

(65) Prior Publication Data

US 2022/0073579 A1 Mar. 10, 2022

Related U.S. Application Data

(63) Continuation of application No. 13/419,045, filed on Mar. 13, 2012, now abandoned.

(60) Provisional application No. 61/452,299, filed on Mar. 14, 2011.

(51) Int. Cl.
*C07K 14/47* (2006.01)

(52) U.S. Cl.
CPC .... *C07K 14/4725* (2013.01); *C07K 2319/036* (2013.01)

(58) Field of Classification Search
CPC .......... C07K 14/4725; C07K 2319/036; A61P 17/00; A61P 17/02; A61P 25/00; A61P 35/00
See application file for complete search history.

(56) References Cited

U.S. PATENT DOCUMENTS

| | | | | |
|---|---|---|---|---|
| 5,567,807 A | | 10/1996 | Craig et al. | |
| 6,046,162 A | * | 4/2000 | Ruoslahti | A61P 43/00 530/395 |
| 6,509,314 B1 | * | 1/2003 | Ruoslahti | C07K 14/4725 514/8.9 |
| 6,852,510 B2 | * | 2/2005 | Bremel | C12N 15/8241 435/456 |
| 8,258,269 B2 | | 9/2012 | Ohigashi | |
| 2003/0124152 A1 | * | 7/2003 | Pang | A61K 8/64 424/94.63 |
| 2005/0160483 A1 | | 7/2005 | Meade et al. | |
| 2010/0145020 A1 | * | 6/2010 | Ohigashi | A61P 7/02 530/381 |

FOREIGN PATENT DOCUMENTS

| | | | |
|---|---|---|---|
| JP | 07-504886 | 6/1995 | |
| JP | 10-506523 | 6/1998 | |
| JP | 2003-532681 | 11/2003 | |
| WO | WO 93/09800 | 5/1993 | |
| WO | WO-9320202 A1 * | 10/1993 | C07K 14/4725 |
| WO | WO 96/01842 | 1/1996 | |
| WO | WO 01/85192 | 11/2001 | |
| WO | WO-2008117735 A1 * | 10/2008 | C07K 1/165 |
| WO | WO 2011/012726 | 2/2011 | |
| WO | WO-2011012726 A2 * | 2/2011 | A61P 7/02 |

OTHER PUBLICATIONS

Singh RK et al. Protein Engineering Approaches in the Post-Genomic Era. 2017. Current Protein and Peptide Science. 18, 1-11. (Year: 2017).*

Zhang M et al. Propagated Perturbations from a Peripheral Mutation Show Interactions Supporting WW Domain Thermostability. 2018. Structure. 26, 1474-1485. (Year: 2018).*

Jarvinen T. et al. "Target-seeking antifibrotic compound enhances wound healing and suppresses scar formation in mice" Proc Natl Arad Sci U S A. Dec. 14, 2010;107(50):21671-6.

Seo, et al., "Decorin core protein secretion is regulated by n-linked oligosaccharide and glycosaminoglycan additions," The Journal of Biological Chemistry, 280(52):42774-427782, Dec. 30, 2005.

Gu, J. et al., "The production and purification of functional decorin in a baculovirus system," Biochem. Biophys. Res. Commun., 1997, vol. 232, No. 1, pp. 91-95.

Mann, D.M. et al., "Analysis of glycosaminoglycan substitution in decorin by site-directed mutagenesis," J. Biol. Chem., 1990, vol. 265, No. 9, pp. 5317-5323.

Davies, J.E., et al., "Decorin Promotes Plasminogen/Plasmin Expression within Acute Spinal Cord Injuries and by Adult Microglia In Vitro", J Neurotrauma 23, 397-408 (2006).

Davies, JE., et al., "Decorin suppresses neurocan, brevican, phosphacan and NG2 expression and promotes axon growth across adult rat spinal cord injuries", Eur. J Neuroscience. 19, 1226-1242 (2004).

Logan, A., et al., "Decorin attenuates gliotic scar formation in the rat cerebral hemisphere," Exp. Neurol. 159, 504-510 (1999).

Ruehland et al. "The glycosaminoglycan chain of decorin plays an important role in collagen fibril formation at the aarly stages of fibrillogenesis" FEBS Journal vol. 274, No. 16, 2007, pp. 4246-4255.

Schmidt et al. "Interaction of the small proteoglycan decorin with fibronectin" Biochem J., 1991, vol. 280, pp. 411-414.

Supplementary European Search Report, EP Patent Application No. 12757556.1, mailed Oct. 23, 2015.

* cited by examiner

*Primary Examiner* — Paul J Holland

(74) *Attorney, Agent, or Firm* — Casimir Jones, S.C.; J. Mitchell Jones

(57) ABSTRACT

The present invention relates to improved decorin compositions and methods of their production.

14 Claims, 3 Drawing Sheets

Specification includes a Sequence Listing.

FIG. 1

Decorin Expression Gene Sequence:

ATGATGTCCTTTGTCTCTCTGCTCCTGGTAGGCATCCTATTCCATGCCACC
CAGGCCGGCCCGTTTCAACAGAGAGGCTTATTTGACTTTATGCTAGAAGAT
GAGGCTGCAGGGATAGGCCCAGAAGTTCCTGATGACCGCGACTTCGAGCCC
TCCCTAGGCCCAGTGTGCCCCTTCCGCTGTCAATGCCATCTTCGAGTGGTC
CAGTGTTCTGATTTGGGTCTGGACAAAGTGCCAAAGGATCTTCCCCCTGAC
ACAACTCTGCTAGACCTGCAAAACAACAAAATAACCGAAATCAAAGATGGA
GACTTTAAGAACCTGAAGAACCTTCACGCATTGATTCTTGTCAACAATAAA
ATTAGCAAAGTTAGTCCTGGAGCATTTACACCTTTGGTGAAGTTGGAACGA
CTTTATCTGTCCAAGAATCAGCTGAAGGAATTGCCAGAAAAAATGCCCAAA
ACTCTTCAGGAGCTGCGTGCCCATGAGAATGAGATCACCAAAGTGCGAAAA
GTTACTTTCAATGGACTGAACCAGATGATTGTCATAGAACTGGGCACCAAT
CCGCTGAAGAGCTCAGGAATTGAAAATGGGGCTTTCCAGGGAATGAAGAAG
CTCTCCTACATCCGCATTGCTGATACCAATATCACCAGCATTCCTCAAGGT
CTTCCTCCTTCCCTTACGGAATTACATCTTGATGGCAACAAAATCAGCAGA
GTTGATGCAGCTAGCCTGAAAGGACTGAATAATTTGGCTAAGTTGGGATTG
AGTTTCAACAGCATCTCTGCTGTTGACAATGGCTCTCTGGCCAACACGCCT
CATCTGAGGGAGCTTCACTTGGACAACAACAAGCTTACCAGAGTACCTGGT
GGGCTGGCAGAGCATAAGTACATCCAGGTTGTCTACCTTCATAACAACAAT
ATCTCTGTAGTTGGATCAAGTGACTTCTGCCCACCTGGACACAACACCAAA
AAGGCTTCTTATTCGGGTGTGAGTCTTTTCAGCAACCCGGTCCAGTACTGG
GAGATACAGCCATCCACCTTCAGATGTGTCTACGTGCGCTCTGCCATTCAA
CTCGGAAACTATAAGTGA

The bovine α-lactalbumin signal peptide coding region is shown in boldface type
The human decorin pro-peptide coding region is underlined
The mutated mature decorin coding region is shown in standard type

FIG. 2

Decorin Expression Protein Sequence:

MMSFVSLLLVGILFHATQAGPFQQRGLFDFMLEDEAAGIGPEVPDDRDFEP
SLGPVCPFRCQCHLRVVQCSDLGLDKVPKDLPPDTTLLDLQNNKITEIKDG
DFKNLKNLHALILVNNKISKVSPGAFTPLVKLERLYLSKNQLKELPEKMPK
TLQELRAHENEITKVRKVTFNGLNQMIVIELGTNPLKSSGIENGAFQGMKK
LSYIRIADTNITSIPQGLPPSLTELHLDGNKISRVDAASLKGLNNLAKLGL
SFNSISAVDNGSLANTPHLRELHLDNNKLTRVPGGLAEHKYIQVVYLHNNN
ISVVGSSDFCPPGHNTKKASYSGVSLFSNPVQYWEIQPSTFRCVYVRSAIQ
LGNYK.

The bovine α-lactalbumin signal peptide is shown in boldface type
The human decorin pro-peptide is underlined The mutated mature decorin coding region is shown in standard type (Amino acid #4 of mature decorin was mutated from a serine to an alanine to prevent addition of the GAG moiety to the mature protein. This amino acid is shown in boldface type as well as underlined)

DECORIN COMPOSITIONS AND USE THEREOF

CROSS-REFERENCE TO RELATED APPLICATIONS

This application is a continuation of U.S. patent application Ser. No. 13/419,045, filed Mar. 13, 2012, which claims the benefit of U.S. Provisional Patent Application No. 61/452,299, filed Mar. 14, 2011, the entire contents of which are incorporated herein by reference.

FIELD OF THE INVENTION

The present invention relates to improved decorin compositions and methods of their production.

BACKGROUND OF THE INVENTION

Proteoglycans carrying one or more glycosaminoglycan (GAG) chains form a large gene family that may be classified into five groups according to the structural properties of the core protein. One of the groups is the small Leucine-rich proteoglycan family comprised of decorin (DCN), biglycan, fibromodulin and lumican. These are characterized by 40 kDa core proteins that contain Leucine-rich repeats of approximately 12 amino acids. DCN is a prototype of the group and is also referred to as PG-S2, PG40, proteodermatan sulphate and DS-PGII. It contains one dermatan chondroitin sulphate GAG chain covalently linked to a Serine of the mature core protein and is considered to be a multifunctional proteoglycan.

The proposed functions of DCN include, but are not limited to, regulation of collagen fibrillogenesis, maintenance of tissue integrity via binding with fibronectin and thrombospondin, and a reservoir of transforming growth factor β (TGF-β). The latter function of DCN is achieved through its core protein sequestering the growth factor in the extracellular milieu from receptors expressed on the cell surface.

Infusion of decorin into experimental rodent spinal cord injuries has been shown to suppress scar formation and promote axon growth. Decorin has also been shown to have anti-tumorigenic properties in an experimental murine tumor model and is capable of suppressing the growth of various tumor cell lines. There are multiple alternatively spliced transcript variants known for the decorin gene. Mutations in the decorin gene are associated with congenital stromal corneal dystrophy.

What is needed in the art are improved methods of producing decorin, especially for therapeutic use.

SUMMARY OF THE INVENTION

The present invention relates to improved decorin compositions and methods of their production.

Accordingly, in some embodiments, the present invention provides a fusion protein comprising a heterologous signal peptide operably linked to a sequence encoding decorin. In some embodiments, the signal sequence is an alpha-lactalbumin signal sequence. In some embodiments, the alpha lactalbumin sequence is a bovine alpha-lactalbumin signal sequence. In some embodiments, the sequence encoding decorin encodes a decorin core protein. In some embodiments, the decorin core protein comprises a mutation at position 4 of the mature decorin core protein. In some embodiments, the mutation is a serine to alanine mutation.

In some embodiments, the decorin core protein lacks substantial modification by glycosaminoglycans molecules at position 4 of the mature decorin core protein.

In some embodiments, the present invention provides a vector encoding the fusion proteins described above. In some embodiments, the vector comprises a nucleic acid sequence encoding an alpha-lactalbumin signal sequence operably linked to a sequence encoding a decorin core protein.

In some embodiments, the present invention provides a host cell comprising the vectors described above.

In some embodiments, the present invention provides methods of producing a non-gagylated decorin core protein comprising: providing host cells expressing non-gagylated decorin core protein; culturing said host cell so that said non-gagylated decorin core protein is produced; and purifying said non-gagylated decorin core protein. In some embodiments, the non-gagylated decorin core protein is secreted into medium used to culture said host cells. In some embodiments, the purifying comprises contacting said culture medium with an ion exchange medium. In some embodiments, the purifying comprises contacting said culture medium with a hydroxyapatite medium. In some embodiments, the purifying comprises contacting said culture medium with at least one ion exchange medium and at least one hydroxyapatite medium in any order. In some embodiments, the purifying comprises: contacting said culture medium with a cation exchange medium; washing said cation exchange medium; eluting a first decorin-containing eluate from said cation exchange medium; contacting said first decorin-containing eluate with a hydroxyapatite medium; washing said hydroxyapatite medium; eluting a second decorin-containing eluate from said hydroxyapatite medium. In some embodiments, the cation exchange medium is SP-Sepharose FF. In some embodiments, the hydroxyapatite medium is ceramic hydroxyapatite type I. In some embodiments, the methods further comprise further purification of said second decorin-containing eluate with an ion exchange membrane or column. In some embodiments, the ion exchange membrane is a Q ion exchange membrane. In some embodiments, the methods further comprise a viral inactivation step. In some embodiments, the viral inaction step comprises treatment with a surfactant. In some embodiments, the surfactant is Triton X-100. In some embodiments, the methods further comprise a viral filtration step. In some embodiments, the methods further comprise concentrating said decorin. In some embodiments, the non-gagylated decorin core protein is produced by said host cells at a rate of about greater than 1, 5, or 10 pg/cell/day.

In some embodiments, the present invention provides methods for purifying decorin from a decorin-containing medium comprising: contacting said decorin-containing medium with a cation exchange medium; washing said cation exchange medium; eluting a first decorin-containing eluate from said cation exchange medium; contacting said at first decorin-containing eluate with a hydroxyapatite medium; washing said hydroxyapatite medium; eluting a second decorin-containing eluate from said hydroxyapatite medium; filtering said second decorin-containing eluate with an ion exchange membrane to provide a decorin-containing filtrate; treating said filtrate to remove viruses; and concentrating decorin from said filtrate.

In some embodiments, the present invention provides compositions comprising a purified decorin core protein comprising a mutation at position 4 of the mature decorin core protein so that said decorin protein is substantially non-gagylated, said composition comprising less than about 100 ng residual host cell protein/mg decorin core protein in said composition and less than about 20 pg residual host cell DNA/mg decorin core protein. In some embodiments, the compositions comprise less than about 5 ng residual host cell protein/mg decorin core protein in said composition and less than about 5 pg residual host cell DNA/mg decorin core protein. In some embodiments, the decorin is formulated as an aqueous solution. In some embodiments, the aqueous solution comprises a phosphate buffered solution with a pH of from about 6.5 to about 7.5.

DESCRIPTION OF THE FIGURES

FIG. 1: Decorin expression gene sequence (SEQ ID NO:8).

FIG. 2: Decorin expression protein sequence (SEQ ID NO:4).

DEFINITIONS

Figure 3:
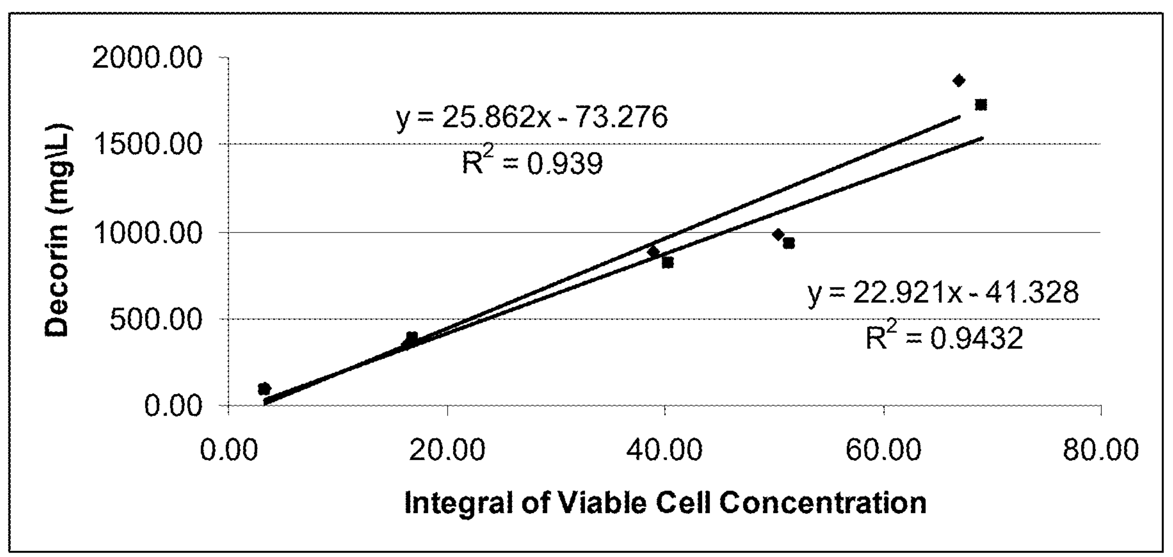
FIG. 3: The integral of viable cell concentration is plotted versus decorin production throughout the 15 day bioreactor run. The slope of the regression line for each run corresponds to the cell productivity in picograms/cell/day (p/c/d). These two runs averaged 24.4 p/c/d. Maximum production reached ~1.8 g/L for one run and 1.7 g/L for the other run.

To facilitate understanding of the invention, a number of terms are defined below.

As used herein, the term "decorin" refers to a protein molecule having a mature protein sequence that is at least 80% identical to SEQ ID NO:4.

As used herein, the term "decorin core protein" refers to a decorin protein molecule that has a mutation at amino acid 4 of mature decorin and that substantially lacks modification with a glycosaminoglycan (GAG; i.e., is non-gagylated) at amino acid 4.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "signal sequence" refers to any DNA sequence which, when operably linked to a recombinant DNA sequence, encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255 (16): 7973-77 [1980], Gray et al., Gene 39 (2): 247-54 [1985], and Martial et al., Science 205:602-607 [1979]). Such secretion signal sequences are preferably derived from genes encoding polypeptides secreted from the cell type targeted for tissue-specific expression (e.g., secreted milk proteins for expression in and secretion from mammary secretory cells). Secretory DNA sequences, however, are not limited to such sequences. Secretory DNA sequences from proteins secreted from many cell types and organisms may also be used (e.g., the secretion signals for t-PA, serum albumin, lactoferrin, and growth hormone, and secretion signals from microbial genes encoding secreted polypeptides such as from yeast, filamentous fungi, and bacteria).

As used herein, the term "purified" refers to molecules, either nucleic or amino acid sequences, that are removed from their normal environment, isolated or separated. An "isolated nucleic acid sequence" is therefore a purified nucleic acid sequence. "Substantially purified" molecules are at least 60% free, preferably at least 75% free, and more preferably at least 90% free from other components with which they are normally associated.

DETAILED DESCRIPTION OF THE INVENTION

The present invention relates to improved decorin compositions and methods of their production, and to the use of decorin for the treatment of patients.

Decorin

Native decorin is a glycoprotein with an attached glycosaminoglycan and an average molecular weight of 90-140 kD. The present invention contemplates the production recombinant decorin. In some preferred embodiments, the decorin is decorin core protein, i.e., a substantially non-gagylated decorin. In some embodiments, the decorin core protein comprises a mutation at amino acid 4 (i.e., the 4$^{th}$ amino acid from the N-terminus) of the mature decorin core protein molecule. In some embodiments, the mutation is a serine to alanine mutation. In some embodiments, the decorin core protein is at least 90%, 95%, 99% or 100% identical to SEQ ID NO: 1 (mature decorin core protein), provided that that the decorin core protein comprises a mutation at amino acid 4 (i.e., the 4$^{th}$ amino acid from the N-terminus) of the mature decorin core protein molecule.

Decorin is commonly expressed as a pre-pro-protein. The present invention provides decorin fusion molecules comprising a heterologous signal sequence in operable association with the decorin pro-peptide and mature peptide sequences. In some embodiments, the heterologous signal polypeptide is an alpha-lactalbumin signal polypeptide. In some embodiments, the alpha-lactalbumin signal polypeptide is a bovine alpha-lactalbumin signal polypeptide. In some embodiments, the heterologous signal polypeptide is at least 80%, 90%, or 100% identical to SEQ ID NO:2. In some embodiments, the propeptide sequence is at least 80%, 90%, or 100% identical to SEQ ID NO:3. In some embodiments, the decorin core protein portion of the fusion polypeptide is at least 90%, 95%, 99% or 100% identical to SEQ ID NO:1 (mature decorin core protein), provided that that the decorin core protein comprises a mutation at amino acid 4 (i.e., the 4$^{th}$ amino acid from the N-terminus) of the mature decorin core protein molecule. In some embodiments, the fusion protein is at least 80%, 90%, 95%, 99% or 100% identical to SEQ ID NO: 4 (signal-propeptide decorin core protein), provided that that the decorin core protein comprises a mutation at amino acid 4 (i.e., the 4$^{th}$ amino acid from the N-terminus) of the mature decorin core protein molecule.

The present invention further provides nucleic acid sequences encoding the fusion proteins, as well as vectors comprising the nucleic acid sequences. In some embodiments, the heterologous signal polypeptide is at least 80%, 90%, or 100% identical to SEQ ID NO:5. In some embodiments, the propeptide sequence is at least 80%, 90%, or 100% identical to SEQ ID NO: 6. In some embodiments, the decorin core protein portion of the fusion polypeptide is at least 90%, 95%, 99% or 100% identical to SEQ ID NO:7 (mature decorin core protein), provided that that the decorin core protein comprises a mutation at amino acid 4 (i.e., the 4$^{th}$ amino acid from the N-terminus) of the mature decorin core protein molecule. In some embodiments, the fusion protein is at least 80%, 90%, 95%, 99% or 100% identical to SEQ ID NO: 8 (signal-propeptide decorin core protein)), provided that that the decorin core protein comprises a mutation at amino acid 4 (i.e., the 4$^{th}$ amino acid from the N-terminus) of the mature decorin core protein molecule.

| SEQ ID NO. | Sequence |
|---|---|
| SEQ ID NO: 1 Decorin core protein | DEAAGIGPEVPDDRDFEPSLGPVCPFRCQCHLRVVQCSDLGLDKVPK DLPPDTTLLDLQNNKITEIKDGDFKNLKNLHALILVNNKISKVSPGAF TPLVKLERLYLSKNQLKELPEKMPKTLQELRAHENEITKVRKVTFNG LNQMIVIELGTNPLKSSGIENGAFQGMKKLSYIRIADTNITSIPQGLPPS LTELHLDGNKISRVDAASLKGLNNLAKLGLSFNSISAVINGSLANTP HLRELHLDNNKLTRVPGGLAEHKYIQVVYLHNNNISVVGSSDFCPPG HNTKKASYSGVSLFSNPVQYWEIQPSTFRCVYVRSAIQLGNYK |
| SEQ ID NO: 2 Alpha-lactalbumin signal sequence | MMSFVSLLLVGILFHATQA |
| SEQ ID NO: 3 Decorin propeptide | GPFQQRGLFDFMLE |
| SEQ ID NO: 4 signal-propeptide-decorin core protein | MMSFVSLLLVGILFHATQAGPFQQRGLFDFMLEDEAAGIGPEVPDDR DFEPSLGPVCPFRCQCHLRVVQCSDLGLDKVPKDLPPDTTLLDLQNN KITEIKDGDFKNLKNLHALILVNNKISKVSPGAFTPLVKLERLYLSKN QLKELPEKMPKTLQELRAHENEITKVRKVTFNGLNQMIVIELGTNPL KSSGIENGAFQGMKKLSYIRIADTNITSIPQGLPPSLTELHLDGNKISR VDAASLKGLNNLAKLGLSFNSISAVDNGSLANTPHLRELHLDNNKLT RVPGGLAEHKYIQVVYLHNNNISVVGSSDFCPPGHNTKKASYSGVSL FSNPVQYWEIQPSTFRCVYVRSAIQLGNYK |
| SEQ ID NO: 5 Alpha-lactalbumin signal sequence | ATGATGTCCTTTGTCTCTCTGCTCCTGGTAGGCATCCTATTCCATG CCACCCAGGCC |
| SEQ ID NO: 6 Decorin propeptide | GGCCCGTTTCAACAGAGAGGCTTATTTGACTTTATGCTAGAA |
| SEQ ID NO: 7 Decorin core protein | GATGAGGCTGCAGGGATAGGCCCAGAAGTTCCTGATGACCGCGA CTTCGAGCCCTCCCTAGGCCCAGTGTGCCCCTTCCGCTGTCAATGC CATCTTCGAGTGGTCCAGTGTTCTGATTTGGGTCTGGACAAAGTG CCAAAGGATCTTCCCCCTGACACAACTCTGCTAGACCTGCAAAAC AACAAAATAACCGAAATCAAAGATGGAGACTTTAAGAACCTGAA GAACCTTCACGCATTGATTCTTGTCAACAATAAAATTAGCAAAGT TAGTCCTGGAGCATTTACACCTTTGGTGAAGTTGGAACGACTTTAT |

-continued

| SEQ ID NO. | Sequence |
|---|---|
| | CTGTCCAAGAATCAGCTGAAGGAATTGCCAGAAAAAATGCCCAA<br>AACTCTTCAGGAGCTGCGTGCCCATGAGAATGAGATCACCAAAGT<br>GCGAAAAGTTACTTTCAATGGACTGAACCAGATGATTGTCATAGA<br>ACTGGGCACCAATCCGCTGAAGAGCTCAGGAATTGAAAATGGGG<br>CTTTCCAGGGAATGAAGAAGCTCTCCTACATCCGCATTGCTGATA<br>CCAATATCACCAGCATTCCTCAAGGTCTTCCTCCTTCCCTTACGGA<br>ATTACATCTTGATGGCAACAAAATCAGCAGAGTTGATGCAGCTAG<br>CCTGAAAGGACTGAATAATTTGGCTAAGTTGGGATTGAGTTTCAA<br>CAGCATCTCTGCTGTTGACAATGGCTCTCTGGCCAACACGCCTCAT<br>CTGAGGGAGCTTCACTTGGACAACAACAAGCTTACCAGAGTACCT<br>GGTGGGCTGGCAGAGCATAAGTACATCCAGGTTGTCTACCTTCAT<br>AACAACAATATCTCTGTAGTTGGATCAAGTGACTTCTGCCCACCT<br>GGACACAACACCAAAAAGGCTTCTTATTCGGGTGTGAGTCTTTTC<br>AGCAACCCGGTCCAGTACTGGGAGATACAGCCATCCACCTTCAGA<br>TGTGTCTACGTGCGCTCTGCCATTCAACTCGGAAACTATAAGTGA |
| SEQ ID NO: 8<br>signal-<br>propeptide-<br>decorin core<br>protein | ATGATGTCCTTTGTCTCTCTGCTCCTGGTAGGCATCCTATTCCATG<br>CCACCCAGGCCGGCCCGTTTCAACAGAGAGGCTTATTTGACTTTA<br>TGCTAGAAGATGAGGCTGCAGGGATAGGCCCAGAAGTTCCTGAT<br>GACCGCGACTTCGAGCCCTCCCTAGGCCCAGTGTGCCCCTTCCGC<br>TGTCAATGCCATCTTCGAGTGGTCCAGTGTTCTGATTTGGGTCTGG<br>ACAAAGTGCCAAAGGATCTTCCCCCTGACACAACTCTGCTAGACC<br>TGCAAAACAACAAAATAACCGAAATCAAAGATGGAGACTTTAAG<br>AACCTGAAGAACCTTCACGCATTGATTCTTGTCAACAATAAAATT<br>AGCAAAGTTAGTCCTGGAGCATTTACACCTTTGGTGAAGTTGGAA<br>CGACTTTATCTGTCCAAGAATCAGCTGAAGGAATTGCCAGAAAAA<br>ATGCCCAAAACTCTTCAGGAGCTGCGTGCCCATGAGAATGAGATC<br>ACCAAAGTGCGAAAAGTTACTTTCAATGGACTGAACCAGATGATT<br>GTCATAGAACTGGGCACCAATCCGCTGAAGAGCTCAGGAATTGA<br>AAATGGGGCTTTCCAGGGAATGAAGAAGCTCTCCTACATCCGCAT<br>TGCTGATACCAATATCACCAGCATTCCTCAAGGTCTTCCTCCTTCC<br>CTTACGGAATTACATCTTGATGGCAACAAAATCAGCAGAGTTGAT<br>GCAGCTAGCCTGAAAGGACTGAATAATTTGGCTAAGTTGGGATTG<br>AGTTTCAACAGCATCTCTGCTGTTGACAATGGCTCTCTGGCCAAC<br>ACGCCTCATCTGAGGGAGCTTCACTTGGACAACAACAAGCTTACC<br>AGAGTACCTGGTGGGCTGGCAGAGCATAAGTACATCCAGGTTGTC<br>TACCTTCATAACAACAATATCTCTGTAGTTGGATCAAGTGACTTCT<br>GCCCACCTGGACACAACACCAAAAAGGCTTCTTATTCGGGTGTGA<br>GTCTTTTCAGCAACCCGGTCCAGTACTGGGAGATACAGCCATCCA<br>CCTTCAGATGTGTCTACGTGCGCTCTGCCATTCAACTCGGAAACTA<br>TAAGTGA |

The decorin polynucleotides of the present invention may be employed for producing decorin polypeptides by recombinant techniques. Thus, for example, the polynucleotide may be included in any one of a variety of expression vectors for expressing a polypeptide. In some embodiments of the present invention, vectors include, but are not limited to, retroviral vectors, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host. In some preferred embodiments, the vectors are retroviral vectors as described in U.S. Pat. Nos. 6,852,510 and 7,332,333 and U.S. pat. Publ. Nos. 200402335173 and 20030224415, all of which are incorporated herein by references in their entirety. In some especially preferred embodiments, the vectors are pseudotyped retroviral vectors.

In particular, some embodiments of the present invention provide recombinant constructs comprising one or more of the sequences as broadly described above (e.g., SEQ ID NO: 8). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NO:8) is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomyces cerivisiae, Schizosaccharomyces pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by retroviral transduction, calcium phosphate transfection, DEAE-Dextran mediated transfection, or electroporation (See e.g., Davis et al. [1986] Basic Methods in Molecular Biology). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y.

In some embodiments of the present invention, following transformation of a suitable host strain and growth of the host strain to an appropriate cell density in media, protein is secreted and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

The present invention also provides methods for recovering and purifying decorin from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments, the present invention provides improved methods for the purification of decorin, especially decorin core protein. In some embodiments, the processes comprise two column chromatography steps and a polishing step.

In some preferred embodiments, cation exchange chromatography is used to capture decorin from medium containing decorin, preferably a clarified medium. In some embodiments, the cation exchange chromatography medium is SP-Sepharose FF. In some embodiments, the cation exchange medium is equilibrated at about 5 to 15 mM sodium phosphate, preferably 10 mM sodium phosphate, and 20 to 70 mM NaCL, preferably about 50 mM NaCL at a neutral pH. In some embodiments, after application of the decorin containing medium to the cation exchange medium, the cation exchange medium is washed. In some embodiments, the wash buffer comprises about 5 to 15 mM sodium phosphate, preferably 10 mM sodium phosphate, and 20 to 70 mM NaCL, preferably about 50 mM NaCL. In some embodiments, decorin is then eluted from the cation exchange medium. In some embodiments, the elution buffer comprises about 5 to 15 mM sodium phosphate, preferably 10 mM sodium phosphate, and 150 to 250 mM NaCL, preferably about 200 mM NaCL.

In some embodiments, the eluate containing decorin from the cation exchange chromatography step is applied to a hydroxyapatite medium. In some embodiments, the hydroxyapatite medium is CHT Type 1. In some embodiments, the hydroxyapatite medium is equilibrated at about 5 to 15 mM sodium phosphate, preferably 10 mM sodium phosphate, and 150 to 250 mM NaCL, preferably about 200 mM NaCL. In some embodiments, after application of the decorin containing medium to the hydroxyapatite medium, the hydroxyapatite medium is washed. In some embodiments, the wash buffer comprises about 5 to 15 mM sodium phosphate, preferably 10 mM sodium phosphate, and 150 to 250 mM NaCL, preferably about 200 mM NaCL. In some embodiments, decorin is then eluted from the hydroxyapatite medium. In some embodiments, the elution buffer comprises about 0.2 to 0.4 M sodium phosphate, preferably 0.3 M sodium phosphate, and 150 to 250 mM NaCL, preferably about 200 mM NaCL.

In some embodiments, the eluate containing decorin from the hydroxyapatite chromatography step is buffer exchanged and applied to an ion exchange membrane. In some embodiments, the ion exchange membrane is a Q ion exchange membrane, for examples a Mustang Q ion exchange medium. In some embodiments, the membrane is equilibrated with from about 30 mM to 70 mM Tris-HCl, preferably about 50 mM Tris-HCl. In some embodiments, after application of the decorin-containing solution to the membrane, the membrane is washed and the decorin passes through the membrane. In some embodiments, the wash buffer comprises from about 30 mM to 70 mM Tris-HCl, preferably about 50 mM Tris-HCl. Following purification, the decorin is preferably concentrated to a desired concentration, for example by flow filtration.

In other embodiments of the present invention, solutions of containing the decorin are treated to inactivate or remove viruses. In some embodiments, solutions comprising decorin are treated with a surfactant to inactivate viruses. In some embodiments, the surfactant is Triton X-100. In some embodiments, the surfactant treating step is performed after the cation exchange chromatography step. In some embodiments, the solutions comprising decorin are filtered to remove viruses. In some embodiments, the solutions are filtered through a viral Filter (e.g., a Virosart viral filter). In some embodiments, the filtrations step is performed after the hydroxyapatite chromatography step.

The processes of the present invention preferably provide decorin compositions suitable for clinical use in human patients. In some embodiments, the compositions comprise a purified decorin core protein comprising a mutation at position 4 of the mature decorin core protein so that the decorin protein is substantially non-gagylated. In some embodiments, the compositions provide purified decorin proteins, and the compositions are characterized in comprising less than about 100, 50, 20, 10, 5 or 2 ng residual host cell protein/mg decorin core protein in the composition and/or less than about 20, 10, 5, or 2 pg residual host cell DNA/mg decorin core protein. In some embodiments, the decorin is provided in a aqueous solution. In some embodiments, the aqueous solution is phosphate buffered saline (e.g., 10 mM sodium phosphate, 150 mM sodium chloride), with a pH of from about 6.5 to 7.5, preferably about 7.0.

EXPERIMENTAL

Example 1

Expression and Production Optimization of a Mutated Form of Human Decorin

An expression construct was produced for a mutant form of Decorin. A serine to alanine modification was made at amino acid 4 of mature Decorin. The mutation prevents a GAG from being attached to the Decorin molecule. The expression construct uses the bovine alpha-lactalbumin signal peptide instead of the endogenous signal peptide for protein production and secretion. The construct is depicted in FIGS. 7 and 8.

To confirm that the expression construct resulted in formation of the correct protein, a CHO cell line was made using the GPEx® process and the above gene construct. Decorin was produced and purified. N-terminal amino acid sequencing was done on the purified protein. The resulting sequence is shown below.

Asp-Glu-Ala-Ala-Gly-Ile-Gly-Pro-Glu-Val-Pro-Asp-Asp-Arg-Asp-Phe-Glu-Pro-Ser-Leu (SEQ ID NO:9)

The sequence corresponds to the expected sequence of the mature protein. The alanine mutation was incorporated as expected and the signal peptide and pro-protein cleaved to yield the correct mature Decorin N-terminal sequence.

Clonal cell lines that produce mutated Decorin were generated using GPEx®. The top expressing cell line was selected by screening different culture conditions and Master cell banked. Production of the cell line was examined in two 10 L bioreactor runs using fed-batch conditions. The results of the run are shown in FIG. 9.

Example 2

Purification of Decorin Core Protein 1.0 Summary

The development of a purification was developed at a small scale and this was applied to One 200 L batch, produced in a GMP suite using fed batch feed strategy. This batch was harvested on day 14 at approximately a 50% viability level. Protein concentration level was 1.240 g/l on day 14 (harvest date) of the bioreactor.

1.1 Components Used in the Synthesis of DCP

The cell culture medium used for all culture steps was HyClone (Logan, UT, USA) HyQ PF-CHO Liquid Soy (LS) with L-glutamine and 0.1% Pluronic F68. The medium was received as a complete, sterile liquid. HyQ PF-CHO LS is a proprietary protein-free cell culture medium formulation from HyClone. The exact ingredients are not known, however, HyClone does hold a Type II Device File for Serum-Free Medium with the FDA for HyQ PF-CHO LS (reference number BBMF8302). HyQ CellBoost R15.4 is proprietary media supplement formulations from HyClone used in the production culture.

| Description | Company | Product Number |
|---|---|---|
| HyQ PF-CHO LS with L-glutamine and 0.1% Pluronic F68 (1 L Bottle) | HyClone | SH30359.02 |
| HyQ PF-CHO LS with L-glutamine and 0.1% Pluronic F68 (30 L Bag) | HyClone | SH3A1568.07 |
| HyQ PF-CHO LS with L-glutamine and 0.1% Pluronic F68 (175 L Bag) | HyClone | SH3A1568.08 |
| HyQ Cell Boost R15.4 Supplement | HyClone | SH30857.03 |

1.2.1 Scale-Up of 200 L Production Culture Inoculum

Details for each subculture step are presented in the Processing Steps for Inoculum Culture Scale-up table below. Production lot 09018 was initiated by thawing a MCB vial, Lot number 06005 (Vial #182) in a 37° C. water bath. After thawing the frozen MCB vial, the cells were added to a single shake flask (250 mL) (Thermo Fisher Scientific) containing 35 mL of HyQ PF-CHO LS cell culture medium. The initial cell count, determined using a hemacytometer, was $2.25\times10^5$ cells/mL and 90.4% viability. The culture was then placed on an Orbit shaker (90 rpm) within an incubator maintained at 37° C. in a humidified, 5% $CO_2$ environment. Subculture steps targeted inoculation densities of approximately $2.0\times10^5$ cells/ml. The day 3 cell count and percent viability in the flask was $14.24\times10^5$ cells/mL with 95.8% viability and the flask was subcultured to 1 L flask. The Day 3 average viable cell count from the 1 L flask was $23.43\times10^5$ cells/mL with 98.1% viability. The 1 L flask was subcultured to a Wave Bioreactor System 20EH with a 10 L disposable Wave Bag (GE Healthcare Bioscience Bioprocess Corp, Somerset, NJ) at an initial culture volume and an initial target cell density of 1000 mL and $2.0\times10^5$ cells/mL, respectively. The Wave Bioreactor operating settings were 37.0° C. incubation temperature, 15.0 cpm rocker speed, 11.0° rocking angle, and 5.0% $CO_2$ concentration in the aeration gas with gas flow rate of 0.25 L/minute. After 2 days the viable cell density in the Wave Bag was $10.28\times10^5$ cells/ml, fresh HyQ PF-CHO LS was added bringing the culture volume to 4992 mL. After three days, the viable cell density was $18.37\times10^5$ cells/mL and the volume in the Wave Bag was transferred to the 30 L bioreactor. The operating set-points in the 30 L bioreactor for temperature, pH, dissolved oxygen, pressure, and agitation rate were 37° C., 40% air saturation, 1 psig pressure, and 50 rpm agitation rate, respectively. The pH controller was not activated, allowing for the cells to naturally drift toward a pH of 7.

Processing Steps for Inoculum Culture Scale-up

| | Subculture Information | |
|---|---|---|
| Step | Inoculum Results | Final Results |
| Vial Thaw/1 × 250 mL Shake Flask | MCB Vial #182<br>VCC: 2.25 × $10^5$ cells/mL<br>Percent Viable Cells: 90.4%<br>Volume = 35 mL | VCC: 14.24 × $10^5$ cells/mL<br>Percent Viable Cells: 95.8%<br>Approx. Final Volume = 34 mL |
| 1 × 1 L Shake Flask | VCC: N/A<br>Percent Viable Cells: N/A<br>Final Volume = 175 mL | VCC: 23.43 × $10^5$ cells/mL<br>Percent Viable Cells: 98.1%<br>Final Volume = 174 mL |
| Wave Bioreactor 10 L Wave Bag | VCC: NA<br>Percent Viable Cells: NA<br>Final Volume = 1000 mL | VCC: 10.28 × $10^5$ cells/mL<br>Percent Viable Cells: 97.2%<br>Final Volume = 992 mL |
| Wave Bioreactor-First Medium Addition Step | VCC: NA<br>Percent Viable Cells: NA<br>Final Volume = 4992 mL | VCC: 18.37 × $10^5$ cells/mL<br>Percent Viable Cells: 99.1%<br>Final Volume = 4984 mL |
| 30 L Bioreactor | Oct. 18, 2009<br>VCC: 3.43 × $10^5$ cells/mL<br>Percent Viable Cells: 98.8%<br>Final Volume = 29.1 L | Oct. 20, 2009<br>VCC: 14.87 × $10^5$ cells/mL<br>Percent Viable Cells: 95.3%<br>Final Volume = 28.1 L |

Abbreviations: VCC, Viable cell count 1.2.2 Culture in 200 L Production Bioreactor Initially, 137 Kg of HyQ PF-CHO LS cell culture medium and 4.3 Kg HyQ Cell Boost R15.4 12% (w/v) solution were added to the 200 L bioreactor. "Day 0" of the production culture was considered the day the 200 L bioreactor was inoculated.

The viable cell density in the 30 L bioreactor was $14.87\times10^5$ cells/mL on day two of culture, which was sufficient to inoculate the 200 L bioreactor at an initial target density of $2.00\times10^5$ cells/mL. The entire contents of the 30 L were transferred and the post inoculum weight, cell density and viability were 171.9 Kg, $2.90\times10^5$ cells/mL and 93.9%, respectively. The operating set-points in the 200 L bioreactor for temperature, pH, dissolved oxygen, pressure, and agitation rate were 37° C., pH 7.0, 40% air saturation, 1 psig pressure, and 35 rpm agitation rate, respectively.

The pH deadband was initially set at actual pH value minus 7.0, prior to inoculation. This was done to prevent the addition of $CO_2$, and allow the cells to naturally drift toward a pH of 7.0. The initial deadband setting was 0.32. After inoculation, the pH was checked daily and the deadband adjusted to actual pH value minus 7.0. On day 1, the pH deadband was decreased to 0.22 and on day three, the deadband was set to 0.05 and remained at this setting for the rest of the run.

The first feed was to occur on day 2 or 3, when the glucose level fell below ≤5 g/l, or on day 3 by default. On day 2, glucose level fell below 5 g/L, so an additional 4.4 kg (L) of 12% w/v HyQ Cell Boost R15.4+120 mM L-glutamine solution was added to the bioreactor. The next feed was to occur on day 4 or 5, when the glucose level fell below ≤5 g/L. On day 4, the glucose level fell below 5 g/L which triggered an additional feed of 9 g/L (14.2 L) of 12% w/v HyQ Cell Boost R15.4 solution. On day 5, the temperature was reduced from 37° C. to 31° C. Day 6 through harvest, the glucose level was checked daily and the addition of a 20% glucose solution to yield a 3 g/L increase in glucose was to occur on any day the glucose level fell below ≤5 g/L. On day 8 and 12, the glucose level fell to 4.84 and 4.98 g/l, respectively. On day 8 and 12, 2.9 and 3.0 kg (L) of 20% glucose solution was added to the bioreactor.

The viable cell density peaked on day 5 at $61.00\times10^5$ cells/mL with a viability of 95.7%. The bioreactor was harvested on Nov. 3, 2009, (day 14) at a cell viability of 50.2%, with a final weight of the bioreactor at 191.8 Kg.

The integrated cell number (ICN) was generated and plotted against protein results to give a curve of which the slope gives the pcd (27.316) for the 14 day run.

1.4 Summary of Upstream Production

This lot was harvested on day 14, at a viability of 50.2% and a titer of 1.240 g/L. The batch was transferred to downstream and purified per the downstream batch processing record.

DCP 200 L Downstream Purification 1.3 Summary

The harvested material from the 200 L batch was purified as outlined below resulting in 211 g (at 5 mg/mL) in a final volume of 42 L. The final bulk drug substance met the specifications previously approved for this batch. All concentrations were determined by absorbance unless otherwise stated.

1.4 Clarification (Nov. 3, 2009)

The harvest material (189 L) was filtered through a Cuno 60M02 Maximizer filter (2×16 $ft^2$) at a volume/area of 5.9 L/$ft^2$ at an initial flow rate of 3 L/min and through a 0.22 μm 10" Millipore Opticap filter. The filter housing was blown down with compressed nitrogen to maximize product recovery.

TABLE 1

| Analysis of Clarification Step | | | | |
|---|---|---|---|---|
| Step | Volume (L) | Protein* mg/mL | Total Protein (g) | % Recovery |
| Media | 189.3 | 1.24 | 235 | 100 |
| Clarified Media | 190.7 | 1.39 | 265 | 113 |

*concentration based on RP-HPLC.

1.5 Capture—Cation Exchange Chromatography

SP-Sepharose FF (GE Healthcare) was used for the capture of the protein from the clarified media. The clarified media was diluted to reduce the conductivity prior to capture on to the column. The conditions of this run are shown below along with the analysis of the various fractions. The clarified media was processed as two sub batches.

TABLE 2

| SP-Sepharose Column Parameters | |
|---|---|
| Matrix | SP-Sepharose FF (GE Healthcare) |
| Column | BPG300 |
| Column Height (cm) | 15 |
| Column Cross Sectional Area ($cm^2$) | 688 |
| Column Diameter (cm) | 30 |
| Column Volume (L) | 10.3 |
| Maximum Load Capacity (mg/mL resin) | 20 |
| Load | Diluted Clarified Media |
| Flow rate | 2.29 L/min, 200 cm/hr 3 minute contact time |
| Actual Load (mg/mL resin)-Sub Batch A | 12.9 |
| Actual Load (mg/mL resin)-Sub Batch B | 12.8 |

Capture-SP-Sepharose Sub Batch A

TABLE 3

| SP-Sepharose Process Conditions | | | |
|---|---|---|---|
| Step Description | Solution Description | Column Volumes (CV) | Actual Volume (L) |
| Sanitization | 1M NaOH | 3 | 32 |
| Charge | 10 mM sodium phosphate, 1M NaCl, pH 7.0 | 3 | 39 |
| Equilibrate | 10 mM sodium phosphate, 50 mM NaCl, pH 7.0 | 5 | 54 |
| Load | Clarified Media diluted with 2 volumes of water (Conductivity = 6.31 mS/cm) | — | 286.1 |
| Wash | 10 mM sodium phosphate, 50 mM NaCl, pH 7.0 | 5 | 54 |
| Elute | 10 mM sodium phosphate, 200 mM NaCl, pH 7.0 | Approx. 2.5 | 35.2 |
| Strip | 10 mM sodium phosphate, 1M NaCl, pH 7.0 | 2 | 22.5 |
| Clean | 1M NaOH | 2 | 22.5 |
| Storage | 0.01M NaOH | 2 | 22.5 |

TABLE 4

| SP-Sepharose Sub-Lot A Fractions | | | | |
|---|---|---|---|---|
| Fraction | Volume (L) | Protein mg/mL | Total Protein (g) | Recovery (%) |
| Load | 95.4 | 1.39* | 133 | 100 |
| SP Sub Lot A Pool | 35.2 | 4.15 (4.11** ) | 146 | 110 |

*this concentration was determined using RP-HPLC, pre dilution.
**measured by Reversed Phase HPLC

1.5.1 Capture-SP-Sepharose Sub Batch B

TABLE 5

| SP-Sepharose Sub Batch B Process Conditions | | | |
|---|---|---|---|
| Step Description | Solution Description | Column Volumes (CV) | Actual Volume (L) |
| Sanitization | 1M NaOH | 3 | 32 |
| Charge | 10 mM sodium phosphate, 1M NaCl, pH 7.0 | 3 | 32 |
| Equilibrate | 10 mM sodium phosphate, 50 mM NaCl, pH 7.0 | 5 | 54 |
| Load | Clarified Media diluted with 2 volumes of water (Conductivity = 6.35 mS/cm) | — | 284.5 |
| Wash | 10 mM sodium phosphate, 50 mM NaCl, pH 7.0 | 5 | 53 |
| Elute | 10 mM sodium phosphate, 200 mM NaCl, pH 7.0 | Approx. 2.5 | 35.6 |
| Strip | 10 mM sodium phosphate, 1M NaCl, pH 7.0 | 2 | 22.9 |
| Clean | 1M NaOH | 2 | 22.9 |
| Storage | 0.01M NaOH | 2.5 | 27.5 |

TABLE 6

| Analysis of SP-Sepharose Sub Lot B Fractions | | | | |
|---|---|---|---|---|
| Fraction | Volume (L) | Protein mg/mL | Total Protein (g) | Recovery (%) |
| Load * | 94.8 | 1.39* | 132 | 100 |
| SP Sub Lot B Pool | 35.6 | 4.20 (4.07**) | 150 | 114 |

*this concentration was determined using RP-HPLC, pre dilution.
**measured by Reversed Phase HPLC

1.6 Viral Inactivation

The two SP-Sepharose sub lots were individual subjected to viral inactivation using 11% (w/v) Triton X-100 diluted to a concentration of 1%. The volumes were incubated at room temperature, with gentle mixing, for 60-90 minutes prior to CHT chromatography. Subsequent processing of the viral inactivated material occurred in the ISO 7 suite.

TABLE 7

| Viral Inactivation Details | | |
|---|---|---|
| | Sub-Lot A | Sub Lot B |
| Initial Volume (L) | 34.66 | 35.42 |
| 11% Triton Addition Volume (L) | 3.47 | 3.54 |
| Final Volume (L) | 38.14 | 38.98 |
| Incubation (mins) | 69 | 61 |

1.7 Intermediate-Ceramic Hydroxyapatite (CHT) Chromatography

CHT Type I (BioRad) was used to further purify DCP from residual CHO protein in the SP-Sepharose pools as well as to remove the Triton from the inactivation step. The conditions of this run are shown below along with the analysis of the various fractions. The SP-Sepharose pools were processed as two sub-batches as described above.

TABLE 8

| CHT Type I Column Parameters | |
|---|---|
| Matrix | CHT Type I 40 μm (BioRad) |
| Column | BPG300 |
| Column Height (cm) | 14 |
| Column Cross Sectional Area ($cm^2$) | 688 |
| Column Diameter (cm) | 30 |
| Column Volume (L) | 9.63 |
| Maximum Load Capacity (mg/mL resin) | 20 |
| Load | Viral Inactivated SP Pool |
| Flow rate | 2.29 L/min, 200 cm/hr 3 minute contact time |
| Actual Load (mg/mL resin)—Sub Batch A | 15.2 |
| Actual Load (mg/mL resin)—Sub Batch B | 15.6 |

1.7.1 CHT Sub Batch A

TABLE 9

CHT Process Conditions

| Step Description | Solution Description | Column Volumes (CV) | Actual Volume (L) |
|---|---|---|---|
| Sanitization | 1M NaOH | 3 | 29.8 |
| Charge | 400 mM sodium phosphate, pH 7.0 | 4 | 41.2 |
| Regeneration | 10 mM sodium phosphate, 1M NaCl, pH 7.0 | 5 | 48 |
| Equilibrate | 10 mM sodium phosphate, 200 mM NaCl, pH 7.0 | 5 | 49.5 |
| Load | Viral Inactivated SP Pool Sub Lot A | — | 37.6 |
| Wash | 10 mM sodium phosphate, 200 mM NaCl, pH 7.0 | 10 | 97 |
| Elute | 0.3M sodium phosphate, 200 mM NaCl, pH 7.0 | Approx. 2.5 | 23.7 |
| Strip | 400 mM sodium phosphate, pH 7.0 | 3 | 29.2 |
| Clean | 1M NaOH | 2 | 22.5 |
| Storage | 0.01M NaOH | 2 | 22.5 |

TABLE 10

CHT Sub-Lot A Fractions

| Fraction | Volume (L) | Protein mg/mL | Total Protein (g) | Recovery (%) | HCP ng/ml | HCP ng/mg |
|---|---|---|---|---|---|---|
| Load* | 35.2 | 4.15* | 146 | 100 | 677 | 163 |
| CHT Sub Lot A Pool | 23.74 | 5.59 (5.28**) | 133 | 91 | 415 | 74 |

*this concentration was determined from the SP-Sepharose pools prior to Triton inactivation.
**measured by Reversed Phase HPLC 1.7.2 Intermediate-CHT Sub Batch B

TABLE 11

CHT Sub Batch B Process Conditions

| Step Description | Solution Description | Column Volumes (CV) | Actual Volume (L) |
|---|---|---|---|
| Sanitization | 1M NaOH | 3 | 30 |
| Charge | 400 mM sodium phosphate, pH 7.0 | 4 | 40 |
| Regeneration | 10 mM sodium phosphate, 1M NaCl, pH 7.0 | 5 | 48 |
| Equilibrate | 10 mM sodium phosphate, 200 mM NaCl, pH 7.0 | 5 | 49.5 |
| Load | Viral Inactivated SP Pool Sub Lot A | — | 39.0 |
| Wash | 10 mM sodium phosphate, 200 mM NaCl, pH 7.0 | 10 | 96.7 |
| Elute | 0.3M sodium phosphate, 200 mM NaCl, pH 7.0 | Approx. 2.5 | 24.44 |
| Strip | 400 mM sodium phosphate, pH 7.0 | 3 | 29.3 |
| Clean | 1M NaOH | 2 | 20.3 |
| Storage | 0.01M NaOH | 2 | 22.5 |

TABLE 12

Analysis of CHT Sub Lot B Fractions

| Fraction | Volume (L) | Protein mg/mL | Total Protein (g) | Re-covery (%) | HCP ng/mL | HCP ng/mg |
|---|---|---|---|---|---|---|
| Load* | 35.6 | 4.20* | 150 | 100 | 743 | 177 |
| CHT Sub Lot B Pool | 24.44 | 5.47 (5.32**) | 134 | 89 | 434 | 79 |

*this concentration was determined from the SP-Sepharose pools prior to Triton inactivation.
**measured by Reversed Phase HPLC 1.8 Intermediate Buffer Exchange of CHT Pools The two CHT pools (47.8 L) were combined and diluted with an equal volume of water giving a total volume of 95.6 L. This was concentrated ~2 fold to ~45 L and approximately ~6.57 mg/mL, using a 0.6 $m^2$ Prep/Scale TFF cartridge (Millipore), 10KMWCO. The re-circulation flow rate was 5 L/min and a back pressure of approximately 20 psi was maintained.

The concentrate was then continuously diafiltered against 7.9 volumes of 25 mM Tris-HCl pH7.5. (55.5 L) and the permeate conductivity at the end of the buffer exchange was confirmed to be at <5 mS/cm (4.40 mS/cm). The filter was washed and this and the concentrate were combined and 0.2 μm filtered prior to storage at 2-8° C.

TABLE 13

Intermediate Buffer Exchanged Fractions

| Fraction | Volume (L) | mg/mL Protein | Total Protein (g) | Recovery (%) |
|---|---|---|---|---|
| CHT Pool A and B* | 47.8 | 5.54* | 265 | 100 |
| Buffer Exchanged Pool | 38.8 | 6.20 | 241 | 91 |

*this concentration was determined from combining the data from the two CHT pools.

1.9 Polishing—Mustang Q Filtration

The Mustang Q (Pall) step was carried out in flow through mode, with any bound material being eluted with a sodium chloride strip. The Buffer exchanged pool was loaded directly onto the conditioned Mustang Q membrane.

TABLE 14

| Mustang Q Membrane Parameters | |
|---|---|
| Matrix | Mustang Q (Pall) |
| Filter | NP8 |
| Bed Volume (mL) | 780 |
| Maximum Load Capacity (g/mL filter volume) | 0.5 |
| Load | Buffer Exchanged CHT Pool 6.2 mg/mL |
| Flow rate | 2.6 L/min, 3.33 cv/minute |
| Actual Load (mg/mL resin) | 0.32 |

TABLE 15

Mustang Q Process Conditions

| Step Description | Solution Description | Column Volumes (CV) | Actual Volume (L) |
|---|---|---|---|
| Sanitization | 1M NaOH | 12 | 10.4 |
| Charging | 50 mM Tris-HCl, 1M NaCl pH7.5 | 12 | 10.4 |
| Equilibrate | 50 mM Tris-HCL, pH7.5 | 35 | 27.5 |
| Load | Buffer Exchanged CHT Pool | — | 38.8 |
| Wash | 50 mM Tris-HCL, pH7.5 | ~10 | 7.5 |
| Clean | 50 mM Tris-HCl, 1M NaCl pH7.5 | 10 | 7.5 |

TABLE 16

Analysis of Mustang Q Fractions

| Fraction | Volume (L) | Protein mg/mL | Total Protein (g) | Recovery (%) | HCP ng/mL | HCP ng/mg |
|---|---|---|---|---|---|---|
| Mustang Q Load | 38.84 | 6.2 | 241 | 100 | 198 | 32 |
| Mustang Q Pool | 46.18 | 4.75 | 219 | 91 | 11 | 2.3 |

1.10 Viral Filtration

The Mustang Q pool was viral filtered using a Virosart filter.

TABLE 17

| Viral Filter Parameters | |
|---|---|
| Filter | Virosart CPV (Sartorius) |
| Filter Size (inch) | 10 |
| Filter Area ($cm^2$) | 7000 |
| Load | Mustang Q Pool (4.75 mg/mL-46 L) |
| Volume/area ($mL/cm^2$) | 6.6 (31.2 $mg/cm^2$) |
| Pressure | 30 psi Compressed Nitrogen |

The filter was wetted with 3 L of water for injection (WFI) at 30 psi nitrogen.

The Mustang Q pool was passed through the filter under 30 psi nitrogen. The filter was then flushed with 5 L of WFI.

TABLE 18

Analysis of Viral Filtration Fractions

| Fraction | Volume (L) | Protein mg/mL | Total Protein (g) | Recovery (%) |
|---|---|---|---|---|
| Viral Load | 46 | 4.75 | 219 | 100 |
| Viral Filtrate | 48.0 | 4.22 | 203 | 93 |

1.11 Concentration and Formulation

The Viral Filtrate (48.0 L) was concentrated buffer exchanged, using 2×0.6 $m^2$ Prep/Scale TFF cartridge (Millipore), 10KMWCO. The re-circulation flow rate was 5 L/min and a feed pressure of 20 psi was maintained.

The viral filtrate was continuously diafiltered against 6.9 volumes of 10 mM sodium phosphate, 150 mM sodium chloride, pH 7.0 to a final volume of 48.5 L. This bulk was then concentrated down to approximately 40 L and then the cartridge was flushed with 2.4 L of 10 mM sodium phosphate, 150 mM sodium chloride, pH 7.0, to remove any remaining protein. This was pooled with the concentrate and the concentration determined to be 5.0 g/L (42.2 L total volume). The final bulk was then filtered into a bag with a 0.2 μm filter.

TABLE 19

Analysis of Formulation Samples

| | Volume (L) | Protein mg/mL | Total Protein (g) | % Recovery |
|---|---|---|---|---|
| Adjusted Viral Filtrate | 47.8 | 4.22 | 202 | 100 |
| Final filtered Formulated BDS | 42.2 | 5.0* | 211 | 104 |

*measured by QC

2 Step Recovery Table

The table below shows the step recovery of each of the steps used in the purification of this batch Note: these values do not account for viral validation sampling.

TABLE 20

Analysis of Formulation Samples

| Step | Step recovery (%) | Overall Recovery (%) |
|---|---|---|
| Harvest | 100 | 100 |
| Clarification | 113 | 113 |
| SP-Sepharose | 110/114 = 112 | 127 |
| CHT | 91/89 = 90 | 114 |
| Intermediate Buffer Exchange | 91 | 104 |
| Mustang Q | 91 | 95 |
| Viral filtration | 93 | 88 |
| Bulk Drug | 104 | 91 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

What is claimed is:

1. A method of producing a non-gagylated decorin core protein comprising:

providing host cells expressing non-gagylated decorin core protein from a retroviral vector, wherein said non-gagylated decorin core protein is encoded by a nucleic acid sequence that is at least 95% identical to SEQ ID NO:7;

culturing said host cell so that said non-gagylated decorin core protein is produced; and purifying said non-gagylated decorin core protein to provide a decorin core protein composition comprising less than 100 ng residual host cell protein/mg decorin core protein in said composition and less than 20 pg residual host cell DNA/mg decorin core protein.

2. The method of claim 1, wherein said non-gagylated decorin core protein is secreted into medium used to culture said host cells.

3. The method of claim 1, wherein said purifying comprises contacting said culture medium with an ion exchange medium.

4. The method of claim 1, wherein said purifying comprises contacting said culture medium with a hydroxyapatite medium.

5. The method of claim 1, wherein said purifying comprises contacting said culture medium with at least one ion exchange medium and at least one hydroxyapatite medium in any order.

6. The method of claim 1, wherein said purifying comprises:

contacting said culture medium with a cation exchange medium;

washing said cation exchange medium;

eluting a first decorin-containing eluate from said cation exchange medium;

contacting said first decorin-containing eluate with a hydroxyapatite medium;

washing said hydroxyapatite medium;

eluting a second decorin-containing eluate from said hydroxyapatite medium.

7. The method of claim 6, wherein said cation exchange medium is SP-Sepharose FF.

8. The method of claim 6, wherein said hydroxyapatite medium is ceramic hydroxyapatite type I.

9. The method of claim 6, further comprising further purification of said second decorin-containing eluate with an ion exchange membrane or column.

10. The method of claim 9, wherein said ion exchange membrane is a Q ion exchange membrane.

11. The method of claim 6, further comprising a viral inactivation step.

12. The method of claim 6, further comprising a viral filtration step.

13. The method of claim 1, wherein said non-gagylated decorin core protein is produced by said host cells at a rate of about greater than 5 pg/cell/day.

14. The method of claim 1, further comprising formulating the purified decorin core protein composition in an aqueous buffer suitable for administration to humans.

* * * * *

SEQUENCE LISTING

<160> NUMBER OF SEQ ID NOS: 9

<210> SEQ ID NO 1
<211> LENGTH: 329
<212> TYPE: PRT
<213> ORGANISM: Artificial Sequence
<220> FEATURE:
<223> OTHER INFORMATION: Synthetic

<400> SEQUENCE: 1

Asp Glu Ala Ala Gly Ile Gly Pro Glu Val Pro Asp Asp Arg Asp Phe
1 5 10 15

Glu Pro Ser Leu Gly Pro Val Cys Pro Phe Arg Cys Gln Cys His Leu
20 25 30

Arg Val Val Gln Cys Ser Asp Leu Gly Leu Asp Lys Val Pro Lys Asp
35 40 45

Leu Pro Pro Asp Thr Thr Leu Leu Asp Leu Gln Asn Asn Lys Ile Thr
50 55 60

Glu Ile Lys Asp Gly Asp Phe Lys Asn Leu Lys Asn Leu His Ala Leu
65 70 75 80

Ile Leu Val Asn Asn Lys Ile Ser Lys Val Ser Pro Gly Ala Phe Thr
85 90 95

Pro Leu Val Lys Leu Glu Arg Leu Tyr Leu Ser Lys Asn Gln Leu Lys
100 105 110

Glu Leu Pro Glu Lys Met Pro Lys Thr Leu Gln Glu Leu Arg Ala His
115 120 125

Glu Asn Glu Ile Thr Lys Val Arg Lys Val Thr Phe Asn Gly Leu Asn
130 135 140

Gln Met Ile Val Ile Glu Leu Gly Thr Asn Pro Leu Lys Ser Ser Gly
145 150 155 160

Ile Glu Asn Gly Ala Phe Gln Gly Met Lys Lys Leu Ser Tyr Ile Arg
165 170 175

Ile Ala Asp Thr Asn Ile Thr Ser Ile Pro Gln Gly Leu Pro Pro Ser
180 185 190

Leu Thr Glu Leu His Leu Asp Gly Asn Lys Ile Ser Arg Val Asp Ala
195 200 205

Ala Ser Leu Lys Gly Leu Asn Asn Leu Ala Lys Leu Gly Leu Ser Phe
210 215 220

Asn Ser Ile Ser Ala Val Asp Asn Gly Ser Leu Ala Asn Thr Pro His
225 230 235 240

Leu Arg Glu Leu His Leu Asp Asn Asn Lys Leu Thr Arg Val Pro Gly
245 250 255

Gly Leu Ala Glu His Lys Tyr Ile Gln Val Val Tyr Leu His Asn Asn
260 265 270

Asn Ile Ser Val Val Gly Ser Ser Asp Phe Cys Pro Pro Gly His Asn
275 280 285

Thr Lys Lys Ala Ser Tyr Ser Gly Val Ser Leu Phe Ser Asn Pro Val
290 295 300

Gln Tyr Trp Glu Ile Gln Pro Ser Thr Phe Arg Cys Val Tyr Val Arg
305 310 315 320

Ser Ala Ile Gln Leu Gly Asn Tyr Lys
325

<210> SEQ ID NO 2
<211> LENGTH: 19
<212> TYPE: PRT

<213> ORGANISM: Artificial Sequence
<220> FEATURE:
<223> OTHER INFORMATION: Synthetic

<400> SEQUENCE: 2

```
Met Met Ser Phe Val Ser Leu Leu Leu Val Gly Ile Leu Phe His Ala
1               5                   10                  15

Thr Gln Ala
```

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

```
Gly Pro Phe Gln Gln Arg Gly Leu Phe Asp Phe Met Leu Glu
1               5                   10
```

<210> SEQ ID NO 4
<211> LENGTH: 362
<212> TYPE: PRT
<213> ORGANISM: Artificial Sequence
<220> FEATURE:
<223> OTHER INFORMATION: Synthetic

<400> SEQUENCE: 4

```
Met Met Ser Phe Val Ser Leu Leu Leu Val Gly Ile Leu Phe His Ala
1               5                   10                  15

Thr Gln Ala Gly Pro Phe Gln Gln Arg Gly Leu Phe Asp Phe Met Leu
            20                  25                  30

Glu Asp Glu Ala Ala Gly Ile Gly Pro Glu Val Pro Asp Asp Arg Asp
        35                  40                  45

Phe Glu Pro Ser Leu Gly Pro Val Cys Pro Phe Arg Cys Gln Cys His
    50                  55                  60

Leu Arg Val Val Gln Cys Ser Asp Leu Gly Leu Asp Lys Val Pro Lys
65                  70                  75                  80

Asp Leu Pro Pro Asp Thr Thr Leu Leu Asp Leu Gln Asn Asn Lys Ile
                85                  90                  95

Thr Glu Ile Lys Asp Gly Asp Phe Lys Asn Leu Lys Asn Leu His Ala
            100                 105                 110

Leu Ile Leu Val Asn Asn Lys Ile Ser Lys Val Ser Pro Gly Ala Phe
        115                 120                 125

Thr Pro Leu Val Lys Leu Glu Arg Leu Tyr Leu Ser Lys Asn Gln Leu
    130                 135                 140

Lys Glu Leu Pro Glu Lys Met Pro Lys Thr Leu Gln Glu Leu Arg Ala
145                 150                 155                 160

His Glu Asn Glu Ile Thr Lys Val Arg Lys Val Thr Phe Asn Gly Leu
                165                 170                 175

Asn Gln Met Ile Val Ile Glu Leu Gly Thr Asn Pro Leu Lys Ser Ser
            180                 185                 190

Gly Ile Glu Asn Gly Ala Phe Gln Gly Met Lys Lys Leu Ser Tyr Ile
        195                 200                 205

Arg Ile Ala Asp Thr Asn Ile Thr Ser Ile Pro Gln Gly Leu Pro Pro
    210                 215                 220

Ser Leu Thr Glu Leu His Leu Asp Gly Asn Lys Ile Ser Arg Val Asp
225                 230                 235                 240
```

```
Ala Ala Ser Leu Lys Gly Leu Asn Asn Leu Ala Lys Leu Gly Leu Ser
                245                 250                 255

Phe Asn Ser Ile Ser Ala Val Asp Asn Gly Ser Leu Ala Asn Thr Pro
            260                 265                 270

His Leu Arg Glu Leu His Leu Asp Asn Asn Lys Leu Thr Arg Val Pro
        275                 280                 285

Gly Gly Leu Ala Glu His Lys Tyr Ile Gln Val Val Tyr Leu His Asn
    290                 295                 300

Asn Asn Ile Ser Val Val Gly Ser Ser Asp Phe Cys Pro Pro Gly His
305                 310                 315                 320

Asn Thr Lys Lys Ala Ser Tyr Ser Gly Val Ser Leu Phe Ser Asn Pro
                325                 330                 335

Val Gln Tyr Trp Glu Ile Gln Pro Ser Thr Phe Arg Cys Val Tyr Val
            340                 345                 350

Arg Ser Ala Ile Gln Leu Gly Asn Tyr Lys
        355                 360


<210> SEQ ID NO 5
<211> LENGTH: 57
<212> TYPE: DNA
<213> ORGANISM: Artificial Sequence
<220> FEATURE:
<223> OTHER INFORMATION: Synthetic

<400> SEQUENCE: 5

atgatgtcct ttgtctctct gctcctggta ggcatcctat tccatgccac ccaggcc        57


<210> SEQ ID NO 6
<211> LENGTH: 42
<212> TYPE: DNA
<213> ORGANISM: Artificial Sequence
<220> FEATURE:
<223> OTHER INFORMATION: Synthetic

<400> SEQUENCE: 6

ggcccgtttc aacagagagg cttatttgac tttatgctag aa                        42


<210> SEQ ID NO 7
<211> LENGTH: 990
<212> TYPE: DNA
<213> ORGANISM: Artificial Sequence
<220> FEATURE:
<223> OTHER INFORMATION: Synthetic

<400> SEQUENCE: 7

gatgaggctg cagggatagg cccagaagtt cctgatgacc gcgacttcga gccctcccta      60

ggcccagtgt gccccttccg ctgtcaatgc catcttcgag tggtccagtg ttctgatttg     120

ggtctggaca aagtgccaaa ggatcttccc cctgacacaa ctctgctaga cctgcaaaac     180

aacaaaataa ccgaaatcaa agatggagac tttaagaacc tgaagaacct tcacgcattg     240

attcttgtca acaataaaat tagcaaagtt agtcctggag catttacacc tttggtgaag     300

ttggaacgac tttatctgtc caagaatcag ctgaaggaat tgccagaaaa aatgcccaaa     360

actcttcagg agctgcgtgc ccatgagaat gagatcacca aagtgcgaaa agttactttc     420

aatggactga accagatgat tgtcatagaa ctgggcacca atccgctgaa gagctcagga     480

attgaaaatg ggcctttcca gggaatgaag aagctctcct acatccgcat tgctgatacc     540

aatatcacca gcattcctca aggtcttcct ccttccctta cggaattaca tcttgatggc     600

aacaaaatca gcagagttga tgcagctagc ctgaaaggac tgaataattt ggctaagttg     660
```

```
ggattgagtt tcaacagcat ctctgctgtt gacaatggct ctctggccaa cacgcctcat    720

ctgagggagc ttcacttgga caacaacaag cttaccagag tacctggtgg gctggcagag    780

cataagtaca tccaggttgt ctaccttcat aacaacaata tctctgtagt tggatcaagt    840

gacttctgcc cacctggaca caacaccaaa aaggcttctt attcgggtgt gagtcttttc    900

agcaacccgg tccagtactg ggagatacag ccatccacct tcagatgtgt ctacgtgcgc    960

tctgccattc aactcggaaa ctataagtga                                     990
```

<210> SEQ ID NO 8
<211> LENGTH: 1089
<212> TYPE: DNA
<213> ORGANISM: Artificial Sequence
<220> FEATURE:
<223> OTHER INFORMATION: Synthetic

<400> SEQUENCE: 8

```
atgatgtcct ttgtctctct gctcctggta ggcatcctat tccatgccac ccaggccggc     60

ccgtttcaac agagaggctt atttgacttt atgctagaag atgaggctgc agggataggc    120

ccagaagttc ctgatgaccg cgacttcgag ccctccctag gcccagtgtg cccccttccgc    180

tgtcaatgcc atcttcgagt ggtccagtgt tctgatttgg gtctggacaa agtgccaaag    240

gatcttcccc ctgacacaac tctgctagac ctgcaaaaca acaaaataac cgaaatcaaa    300

gatggagact ttaagaacct gaagaacctt cacgcattga ttcttgtcaa caataaaatt    360

agcaaagtta gtcctggagc atttacacct ttggtgaagt tggaacgact ttatctgtcc    420

aagaatcagc tgaaggaatt gccagaaaaa atgcccaaaa ctcttcagga gctgcgtgcc    480

catgagaatg agatcaccaa agtgcgaaaa gttactttca atggactgaa ccagatgatt    540

gtcatagaac tgggcaccaa tccgctgaag agctcaggaa ttgaaaatgg ggctttccag    600

ggaatgaaga agctctccta catccgcatt gctgatacca atatcaccag cattcctcaa    660

ggtcttcctc cttcccttac ggaattacat cttgatggca acaaaatcag cagagttgat    720

gcagctagcc tgaaaggact gaataatttg gctaagttgg gattgagttt caacagcatc    780

tctgctgttg acaatggctc tctggccaac acgcctcatc tgagggagct tcacttggac    840

aacaacaagc ttaccagagt acctggtggg ctggcagagc ataagtacat ccaggttgtc    900

taccttcata acaacaatat ctctgtagtt ggatcaagtg acttctgccc acctggacac    960

aacaccaaaa aggcttctta ttcgggtgtg agtcttttca gcaacccggt ccagtactgg   1020

gagatacagc catccacctt cagatgtgtc tacgtgcgct ctgccattca actcggaaac   1080

tataagtga                                                           1089
```

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

```
Asp Glu Ala Ala Gly Ile Gly Pro Glu Val Pro Asp Asp Arg Asp Phe
1               5                   10                  15

Glu Pro Ser Leu
            20
```